(12) United States Patent
Viebach et al.

(10) Patent No.: US 10,702,134 B2
(45) Date of Patent: Jul. 7, 2020

(54) DEFLECTION MOVEMENT TRANSMISSION SYSTEM, ENDOSCOPE BENDING CONTROL SYSTEM, AND ENDOSCOPE

(71) Applicant: DIGITAL ENDOSCOPY GmbH, Friedberg (DE)

(72) Inventors: Thomas Viebach, Friedberg (DE); Anh Minh Do, Friedberg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 344 days.

(21) Appl. No.: 15/580,928

(22) PCT Filed: Jun. 9, 2016

(86) PCT No.: PCT/EP2016/063190
§ 371 (c)(1),
(2) Date: Dec. 8, 2017

(87) PCT Pub. No.: WO2016/198538
PCT Pub. Date: Dec. 15, 2016

(65) Prior Publication Data
US 2018/0160883 A1    Jun. 14, 2018

(30) Foreign Application Priority Data
Jun. 10, 2015 (DE) .......... 10 2015 109 170

(51) Int. Cl.
*A61B 1/00* (2006.01)
*A61B 1/005* (2006.01)
(52) U.S. Cl.
CPC ........ *A61B 1/0052* (2013.01); *A61B 1/00039* (2013.01); *A61B 1/0055* (2013.01); *A61B 1/0057* (2013.01); *A61B 1/00066* (2013.01)
(58) Field of Classification Search
None
See application file for complete search history.

(56) References Cited

U.S. PATENT DOCUMENTS

| 7,662,092 B2 | 2/2010 | Miyagi et al. |
| 8,287,449 B2 | 10/2012 | Tanaka |

(Continued)

FOREIGN PATENT DOCUMENTS

| DE | 102013222042 A1 | 4/2015 |
| JP | S56-136524 A | 10/1981 |

(Continued)

OTHER PUBLICATIONS

Office Action issued in Japanese family member Patent Appl. No. 2017-564381, dated Oct. 9, 2018.

(Continued)

*Primary Examiner* — Timothy J Neal
(74) *Attorney, Agent, or Firm* — Greenblum & Bernstein, P.L.C.

(57) ABSTRACT

The invention relates to a deflection movement transmission means including a control pivot member for effecting a deflection movement, and a base body including a ball head on which the control pivot member for effecting a deflection movement is arranged such that a pivot movement of the control pivot member can be performed relative to the base body. The control pivot member includes an inner shell, which is elastic or made of several movable pieces and has an inner surface facing towards the ball head. At the outer surface of the inner shell facing away from the ball head, at least one press-on body is provided, by which the inner shell can be pressed against the base body to lock a deflection position of the control pivot member. The invention further relates to an endoscope and an endoscope bending control means including such a deflection movement transmission means.

11 Claims, 12 Drawing Sheets

(56) References Cited

U.S. PATENT DOCUMENTS

| | | | |
|---|---|---|---|
| 10,076,233 B2 | 9/2018 | Viebach et al. | |
| 2004/0267093 A1 | 12/2004 | Miyagi et al. | |
| 2006/0183974 A1 | 8/2006 | Levy et al. | |
| 2006/0252993 A1* | 11/2006 | Freed | A61B 1/0052 600/146 |
| 2009/0209820 A1* | 8/2009 | Tanaka | A61B 1/0052 600/149 |
| 2010/0004633 A1* | 1/2010 | Rothe | A61M 25/0082 604/528 |
| 2016/0249791 A1 | 9/2016 | Viebach et al. | |

FOREIGN PATENT DOCUMENTS

| | | |
|---|---|---|
| JP | 2008-529647 A | 8/2008 |
| JP | 2009-089955 A | 4/2009 |
| JP | 4323209 B2 | 9/2009 |
| JP | 2011-067381 A | 4/2011 |
| JP | 4690399 B2 | 6/2011 |
| JP | 5161529 B2 | 3/2013 |
| JP | 2016-538029 A | 12/2016 |
| WO | 2015/063053 A1 | 5/2015 |

OTHER PUBLICATIONS

Office Action issued in Japanese family member Patent Appl. No. 2017-564381, dated Jun. 4, 2019.

Search Report issued in International Patent Application No. PCT/EP2016/063190, dated Sep. 14, 2016.

IPRP issued in International Patent Application No. PCT/EP2016/063190, dated Dec. 21, 2017, together with an English-language translation.

\* cited by examiner

DEFLECTION MOVEMENT TRANSMISSION SYSTEM, ENDOSCOPE BENDING CONTROL SYSTEM, AND ENDOSCOPE

The present invention relates to a deflection movement transmission means that transmits a deflection movement effected by a control pivot member to a reaction member. Moreover, the present invention relates to an endoscope bending control means and an endoscope.

Such deflection movement transmission means are extremely versatile. One field of application of the deflection movement transmission means is an endoscope in which a bendable end of a catheter, i.e. a so-called deflecting portion, is moved by pivoting of a control pivot member, wherein the movement of the deflecting portion precisely follows the movement of the control pivot member.

In medical examinations using an endoscope, the transmission of a pivot movement of a control pivot member to a bending movement of the deflecting portion should be as precise as possible. On the other hand, the transmission of a pivot movement of a control pivot member to a bending movement of the deflecting portion should be easily and straightforwardly executable for the operator.

In the course of an examination it may be required that a specific deflection position of the bendable end of the catheter, i.e. the deflecting portion, be maintained for a longer period of time for various reasons (e.g. a detailed examination, sampling, etc.). In order to maintain the specific deflection position of the deflecting portion, the relative position of the pivoted control pivot member can be locked.

Problem to be Solved by the Invention

It is the object of the present invention to provide an improved deflection movement transmission means.

In particular, it is the object of the present invention to provide a deflection movement transmission means in which the relative position of the pivoted control pivot member can be locked in a particularly advantageous manner. Moreover, an improved endoscope bending control means and an improved endoscope shall be provided.

Solution to the Problem

According to the invention, this problem is solved by a deflection movement transmission means comprising the features of claim 1. Advantageous further developments are described in the dependent claims. An endoscope bending control means is set forth in claim 10 and an endoscope is set forth in claim 11.

Thus, the invention relates to a deflection movement transmission means comprising a control pivot member for effecting a deflection movement, and a base body including a ball head on which the control pivot member for effecting a deflection movement is arranged such that a pivot movement of the control pivot member can be performed relative to the base body. The control pivot member includes an inner shell having an inner surface facing towards the ball head. On the outer surface of the inner shell facing away from the ball head, at least one press-on body is provided, by which the inner shell can be pressed against the base body so as to lock a deflection position of the control pivot member.

The inner shell can be elastic or made of segments (i.e. made of several parts) extending along meridians, the segments being movable relative to the ball head.

The press-on body acts on the inner shell and presses at least the region of the inner shell on which the press-on body acts towards the ball head. By the region of the inner shell, which is pressed towards the ball head, abutting against the ball head, a friction brake locking the current relative position of the control pivot member relative to the base body is created.

The control pivot member can comprise a non-elastic outer shell, wherein the at least one press-on body, by means of which the inner shell can be pressed against the base body relative to the outer shell, can be arranged between the inner shell and the outer shell.

Here, the press-on body takes a pressed-on position in which it presses the inner shell towards the ball head, and a non-pressed-on position in which it does not press the inner shell towards the ball head.

Thus, the press-on body can be supported on the outer shell to press the inner shell towards the ball head. In an alternative, the outer shell can have a certain elasticity if it is still ensured that the press-on body supported on the outer shell can press the inner shell towards the ball head.

The press-on body can be in contact with the inner shell and the outer shell, and the outer shell can be movable relative to the inner shell so as to bring, via the press-on body, the inner shell into the position pressed against the base body.

The press-on body quasi includes an outside point for a contact with the outer shell and an inside point for a contact with the inner shell. The press-on body can be inserted in a form-fitting manner on the inner shell and/or on the outer shell. The press-on body can be integrally joined to the inner shell and/or to the outer shell. Combinations thereof are possible.

The inner shell can comprise a pivot lever portion extending away from the ball head, and the outer shell can be movable relative to the inner shell in the direction of the axis of the pivot lever portion, so as to bring, via the press-on body, the inner shell into the position pressed against the base body.

On the one hand, together with the control pivot member, the pivot lever portion of the inner shell can be moved, i.e. pivoted, relative to the ball head. On the other hand, the outer shell is movable relative to the inner shell in the direction of the axis of the pivot lever portion (i.e. vertically). By means of a joint mechanism, the relative movement of the outer shell relative to the inner shell in the direction of the axis of the pivot lever portion can be transformed into a press-on movement towards the ball head of at least that region of the inner shell where the press-on body acts.

The outer shell can have two intrinsically stable end positions when moved along the axis of the pivot lever portion relative to the inner shell. Of these end positions, a first end position corresponds to the non-pressed-on position in which the inner shell is not pressed against the base body, and a second end position corresponds to the pressed-on position in which the inner shell is pressed against the base body.

The at least one press-on body may comprise a toggle lever element that is supported in a pivotable manner on the inside of the outer shell and on the outside of the inner shell. The toggle lever element can be operated in such a way that the inner shell is pressed against the base body to lock a deflection position of the control pivot member.

The toggle lever elements of several press-on bodies can be integrally connected by an elastic ring. The elastic ring can connect the individual press-on bodies designed as toggle lever elements in the latitude direction. Thus, several press-on bodies can act concertedly on various locations between the inside of the outer shell and the outside of the inner shell, so as to press respective portions of the inner shell, on which the corresponding press-on bodies act, against the base body.

The at least one press-on body can form an elastic ring. The press-on body may be formed as a single toggle lever element extending in the latitude direction between the inside of the outer shell and the outside of the inner shell.

The press-on body can be formed of an annular member and a toggle lever element integrally formed on the annular member, wherein the annular member can be seated in a pivotable manner in a groove of an inner surface of the outer shell facing towards the inner shell, the groove being adapted to the annular shape of the annular member, and the tip of the toggle lever element facing away from the annular member can be seated in a V-groove of an outer surface of the inner shell facing towards the outer shell.

Alternatively, the press-on body can be formed of an annular member and a toggle lever element integrally formed on the annular member, wherein the annular member can be seated in a pivotable manner in a groove of an outer surface of the inner shell, facing towards the outer shell, the groove being adapted to the annular shape of the annular member, and the tip of the toggle lever element facing away from the annular member can be seated in a V-groove of an inner surface of the outer shell facing towards the inner shell.

The toggle lever element can be made of toggle lever element segments integrally formed on the annular member. The toggle lever element segments are spaced apart from each other and distributed on the inner circumference of the annular member. The toggle lever element segments can be evenly spaced apart from each other or have different distances from each other. In one embodiment, the intermediate spaces between the toggle lever element segments can be used to pass pulling wires therethrough. The intermediate spaces between the toggle lever element segments can be aligned with the grooves of the outer shell and the inner shell. For example, the press-on body may have ten toggle lever element segments on its annular member. Alternatively, the press-on body can, for example, have four or more or less toggle lever element segments on its annular member. It is even possible that the press-on body comprises only one single toggle lever element segment on its annular member.

A lever mechanism can be fastened to the outer surface of the inner shell facing away from the ball head, the lever mechanism being used to operate the press-on body to press the inner shell against the base body. Here, the press-on body is supported on the inner shell itself and can, like a toggle lever for example, press at least the region of the inner shell, on which the press-on body acts, towards the ball head. Here, it is not necessary to support the outside point of the press-on body on the outer shell since the outside point of the press-on body is supported on the inner shell via a joint or a lever.

The control pivot member can be arranged at the proximal end of the deflection movement transmission means, wherein a bendable body to be deflected is arranged at the distal end of the deflection movement transmission means, pulling wire bodies for deflecting the bendable body to be deflected can be fitted to the control pivot member, and the base member and the control pivot member each have an inner channel through which the bendable body to be deflected can be passed.

With the inner shell, the deflection movement transmission means of the present invention uses an elastic member that acts as a friction component on an inner ball member of a joystick. In this way, the locking of the achieved pivot position of the control pivot member designed as a joystick is effected relative to the base member.

The inner shell can be formed as an elastically deformable bell that is provided with slits, slipped onto the ball head and placed on the ball head, for example, in a snap-fit. The inner shell is movable relative to the ball head.

The operating element for braking the pivot position of the control pivot member relative to the base member can be the outer shell that can be formed as a bell slipped onto the inner shell and is linearly movable with respect to the inner shell.

By means of the press-on body constructed as a rotationally symmetrical ring, the pivot position of the control pivot member can be braked relative to the base member. The press-on body can be formed of an elastic material and have a conical initial shape before the inner shell is pressed towards the ball head. By mechanically moving the outside point of the press-on body relative to the inside point of the press-on body, the press-on body is pivoted between two stable end positions. In the first end position, the outside point of the press-on body is on the proximal side relative to the inside point of the press-on body and the inner shell is not pressed towards the ball head. In the second end position, the outside point of the press-on body is on the distal side relative to the inside point of the press-on body and the inner shell is pressed towards the ball head. Since the outside point of the press-on body is supported on the outer shell, which is less elastic than the inner shell on which the inside point of the press-on body is supported, the outer shell is more stable and the inner shell gives way, at least in the region where the press-on body presses, and is pressed towards the ball head. The imagined diameter of the inner shell in the region where the press-on body abuts decreases upon pressing by the press-on body. The outer shell remains unchanged upon pressing by the press-on body. The outside point or the outer region of the press-on body can be embedded in a recess on the outer shell (on the inside of the outer shell) or ca be otherwise articulated. The inside point or the inner region of the press-on body can be embedded in a recess on the inner shell (on the outside of the inner shell) or can be otherwise articulated. By vertically moving the outer shell relative to the inner shell, the press-on body constructed as an elastic ring can snap back and forth between the two end positions.

The recesses for embedding the press-on body are only an example for anchoring the press-on body on the inside of the outer shell and on the outside of the inner shell. Further embodiments in which the press-on body acts as a joint on the inside of the outer shell and on the outside of the inner shell can also be applied to realize the principle of the invention.

The mode of action of the press-on body is based on the toggle lever principle. This means, the press-on body/bodies is/are arranged in an articulated manner between the outer and the inner shell such that, in the released position, it/they take(s) a position oblique to the equatorial plane of the ball head. When the outer shell is moved, the press-on body/bodies is/are moved into the equatorial plane. In this position, they take up more space and therefore press the elastic inner shell against the ball head. The outer shell is enabled to move slightly beyond this maximally pressed-on position (corresponding to a dead center), so that a stable braked end position is achieved. The advantage of the toggle lever principle consists in that, due to the toggle lever joints, less friction occurs, due to the sinusoidal movement, extremely high forces occur at the dead center and just after the dead center a stable clamping position remains which is used for braking and locking the deflection movement of the control pivot member.

The press-on body does not have to be constructed as a complete ring. It can be made up of ring portions located between the outer shell and the inner shell on an imagined line parallel to the equator of the inner shell. The press-on body can have four or more or less ring portions. The press-on body may even have only one single ring portion.

In this deflection movement transmission means, the bendable body to be deflected can be passed through the control pivot member controlling the deflection movement of the bendable body to be deflected and through the base body. Thus, a deflection movement transmission means is provided, which enables a safe and straightforward handling of a bending movement of a deflecting portion in a very small space. In the deflection movement transmission means, the inner channel can be arranged concentrically in the control pivot member and/or the inner channel can be arranged concentrically in the base body. This does not affect the stability of the device as a whole. Moreover, the inner channel in the control pivot member may comprise a funnel-like insertion opening as insertion aid. This makes it possible to safely guide the body passed therethrough. In the deflection movement transmission means, one, two, three, four or more pulling wires may be provided, the first ends of which are articulated on the control pivot member in a manner equally spaced apart from each other, and the opposite second ends of which are fastened to the distal end portion of the body to be deflected in a corresponding manner equally spaced apart from each other.

The features of the invention can be appropriately combined.

Subsequently, the invention is described in detail by means of examples.

Figure 1:
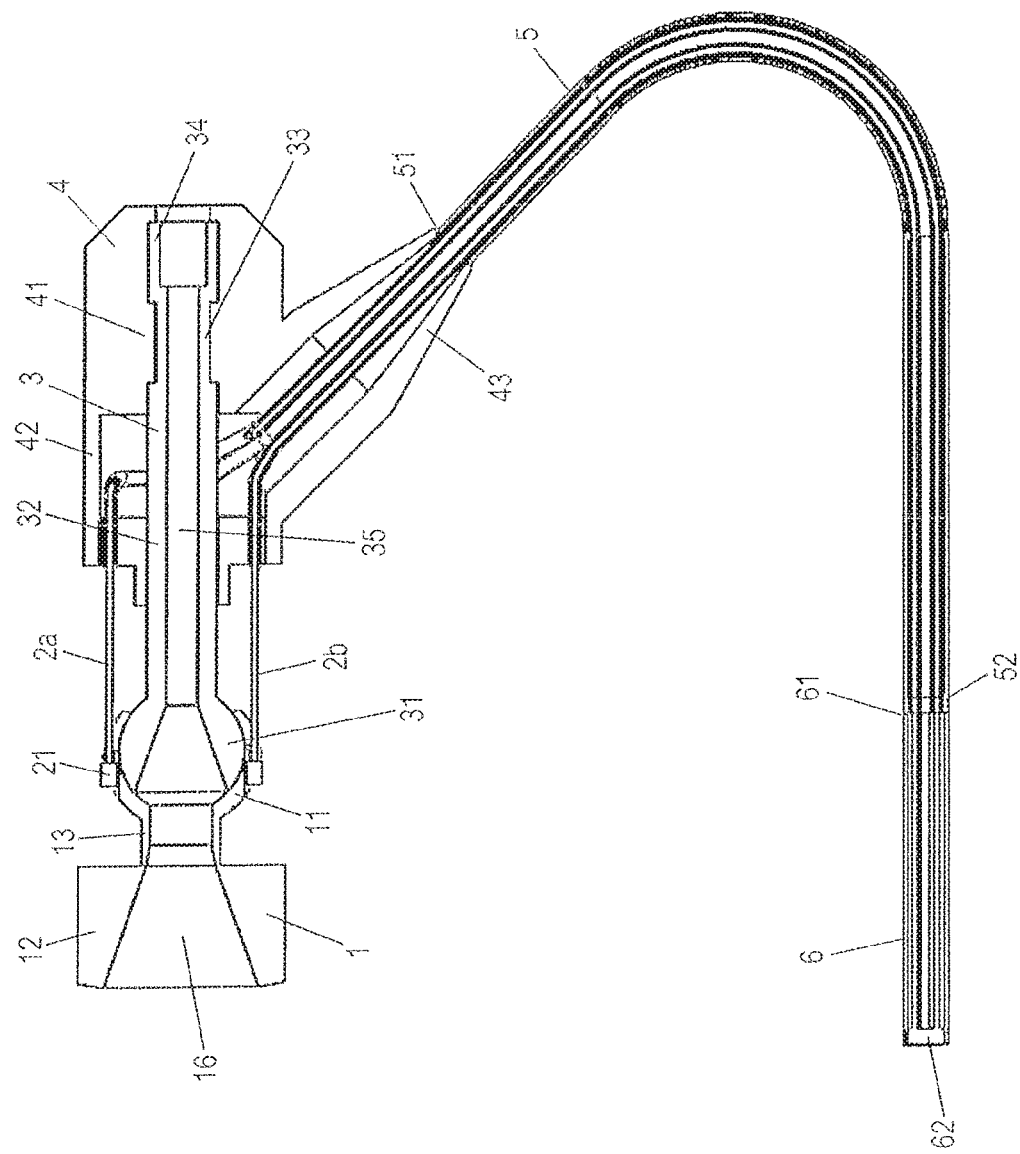
FIG. 1 shows a schematic sectional view of a deflection movement transmission means in a non-deflected state, in which the present invention can be applied.

Subsequently, embodiments of the present invention are described in detail by means of the drawings.

GENERAL DESIGN

First of all, the general design of a deflection movement transmission means used in an endoscope for an endoscope deflecting control is described in detail by using FIGS. 1 to 7.

This deflection movement transmission means consists of a control pivot member 1, several pulling wires 2, a rod element 3 as a base member, a rod element holder 4, a catheter tube 5 and a bendable body as a deflecting portion 6.

The control pivot member 1 consists of a hollow cylindrical element comprising a control head 12, on the bottom side of which a hollow rod 13 is centrically arranged, the hollow rod merging into a hollow ball portion 11 that has the pulling wires 2 anchored to its outer surface. On its side facing away from the head 12, the hollow ball portion 11 is open. In particular, the opening on the hollow ball portion 11 is formed such that the hollow ball portion 11 constitutes about 9/10 of a ball of which about 1/10 is cut off.

The control pivot member 1 is rotationally symmetrically constructed and comprises an inner channel 16 that concentrically extends through the head 12, the hollow rod 13 and the hollow ball portion 11. In the head 12, the inner channel 16 is extended in such a manner that its inner diameter increases towards the side of the head 12 facing away from the hollow ball portion 11, as this is shown in FIG. 1. Thus, the inner channel 16 of the head 12 has a funnel-like insertion opening, which is shown in FIG. 1 on the left side of the inner channel 16. The funnel-like insertion opening of the inner channel 16 facilitates inserting the deflecting portion 6 into the inner channel 16.

The control pivot member 1 is made of a plastic material.

The control pivot member 1 is provided as a joystick on a head 31 of the rod element 3. In particular, the hollow ball portion 11 of the control pivot member 1 is provided on a counter ball portion 31 forming the head of the rod element 3. The counter ball portion 31 is formed such that it has a ball shape of such a size that the hollow ball portion 11 provided thereon can be easily moved. The dimension relations between the counter ball portion 31 and the hollow ball portion 11 are of such a manner that a relative movement of the control pivot member 1 with regard to the rod element 3 is possible without any great effort on the part of the operator and, on the other hand, the hollow ball portion 11 is not provided loosely on the counter ball portion 31.

The rod element 3 comprises a longitudinal cylinder 32 that, on its distal side, makes a transition into the counter ball portion 31 and, on its distal end portion, comprises a screw end 34 that can be formed as an inner square. Distally from the square end 34, the rod element 3 includes an outer threaded portion 33 on its outer cylinder surface. The rod element 3 is constructed rotationally symmetrical and, on its inside, includes an inner channel 35 concentrically extending through the counter ball portion 31, the longitudinal cylinder 32 and the square end 34. Incidentally, the counter ball portion 31, the longitudinal cylinder 32 and the square end 34 are designed as an integral rod element. The longitudinal cylinder 32 of the rod element 3 is formed as a cylinder having a smooth outer surface, except for the threaded portion 33 provided thereon.

On the counter ball portion 31, the inner channel 35 has a funnel-like insertion opening depicted on the left side of the inner channel 35 in FIG. 1. The funnel-like insertion opening of the inner channel 35 opposes the exit opening of the inner channel 16 on the hollow ball portion 11 and facilitates inserting the deflecting portion 6 into the inner channel 35.

As it is shown in the Figures, the rod element 3 is provided in a rod element holder 4. The rod element holder 4 consists of a cylinder element 42 that is rotationally symmetrically designed and comprises a centric inner channel. The cylinder element 42 in particular includes a cavity facing towards the control pivot member 1 and a bottom on the side of the rod element holder 4 facing away from the control pivot member 1. More precisely, the bottom of the rod element holder 4 comprises the concentric inner channel. An inner thread 41 is formed in the concentric inner channel. As this is schematically indicated in the Figures, the outer thread 33 of the rod element 3 is provided on the inner thread 41 of the rod element holder 4; by means of a screwing movement, the rod element 3 can be concentrically screwed in or screwed out relative to the rod element holder 4. For the purpose of performing the screwing movement, an appropriate tool is inserted into the square end 34 of the rod element 3. Other relative movement techniques are possible, as it is described under "Alternatives" at the end of the description.

The cylinder element 42 of the rod element holder 4 has a catheter connecting element 43 on its outer circumferential side. The catheter connecting element 43 extends, for example, at an acute angle relative to the cylinder element 42 of the rod element holder 4, as it becomes clear from the drawings.

In particular, the catheter connecting element 43 is formed as a round hollow profile that practically constitutes a channel branch-off from the distal cavity of the cylinder element 42. The catheter connecting element 43 is designed like a cylinder and tapers in the direction leading away from the cylinder element 42. On the inside, the catheter connecting element 43 has a concentric channel in which the pulling wires 2 are guided. On its distal end, the catheter connecting element 43 has a circular orifice.

The catheter tube 5 is attached to the circular orifice of the catheter connecting element 43. In particular, the proximal end 51 of the catheter tube 5 is provided at the orifice of the catheter connecting element 43. At its distal end, the catheter tube comprises a ring 52 accommodated therein. The ring 52 forms the distal end of the catheter tube and the transition to the deflecting portion 6.

The deflecting portion 6 is a bendable body made of an elastic material in a known manner. At its proximal end, the deflecting portion has a deflecting connection 61 at which it is connected to the ring 52 of the catheter tube 5. At the distal end, the deflecting portion has a deflecting cap 62 on which a camera, a laser and/or a camera, etc. are arranged. Further functional units can be integrated at the deflecting cap 62.

Figure 4:
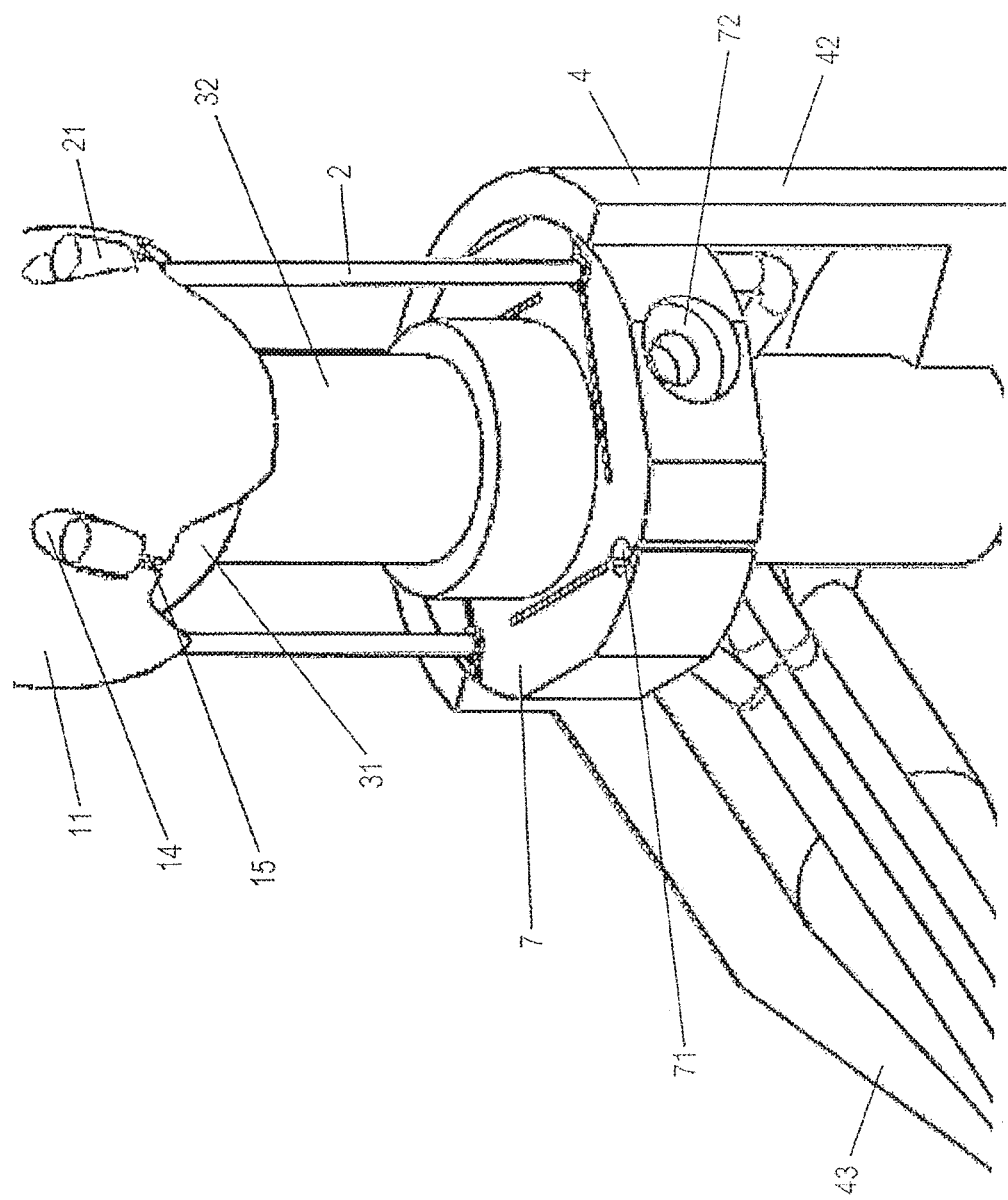
FIG. 4 shows a schematic perspective, extract-like view of details of the attachment of the pulling wires to the control pivot member and how the pulling wires are guided to the catheter tube.
Figure 5:
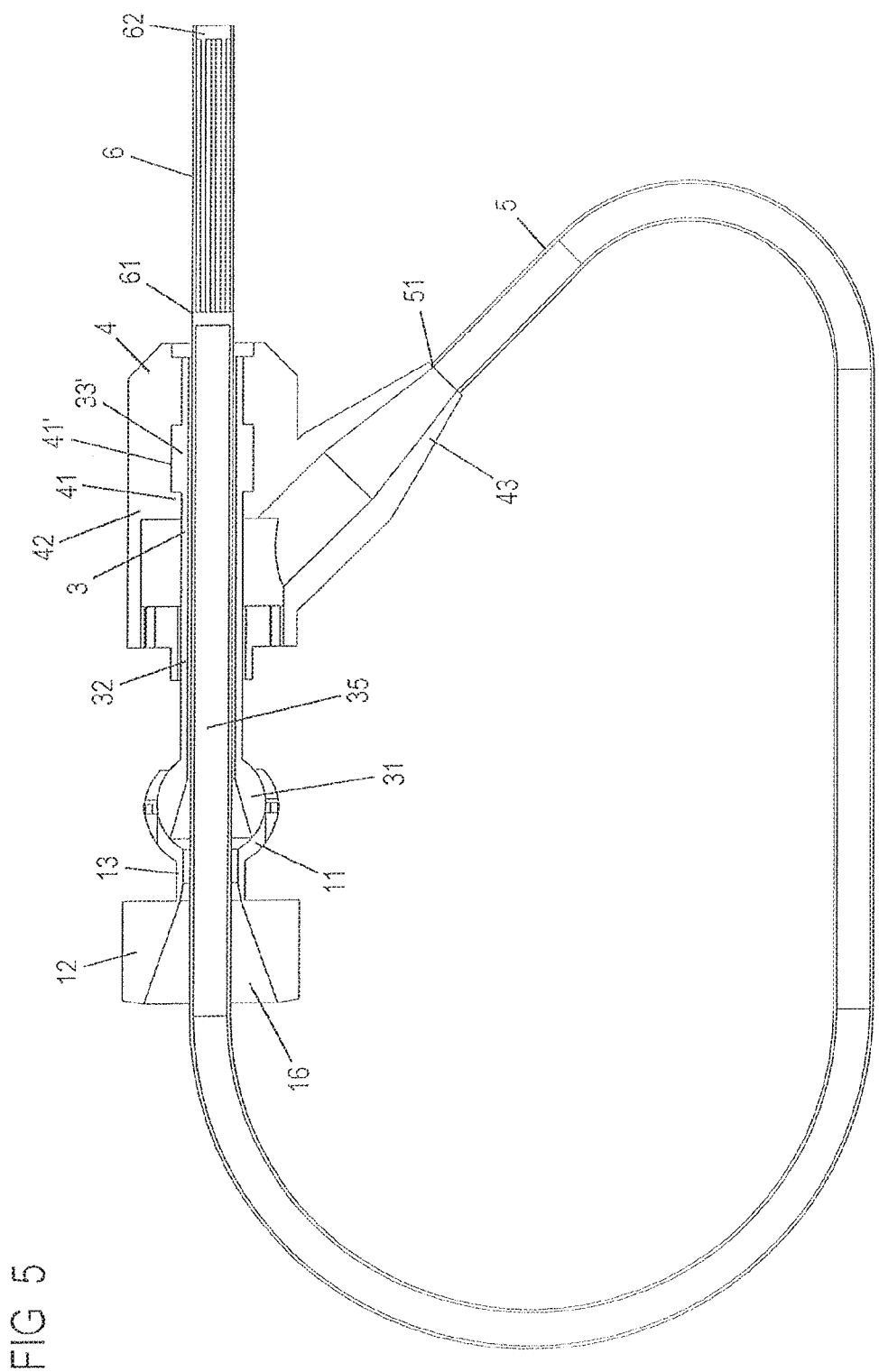
FIG. 5 shows a schematic sectional view of the deflection movement transmission means of FIG. 1 with the catheter tube being passed through the deflection movement transmission means and not being deflected.
Figure 6:
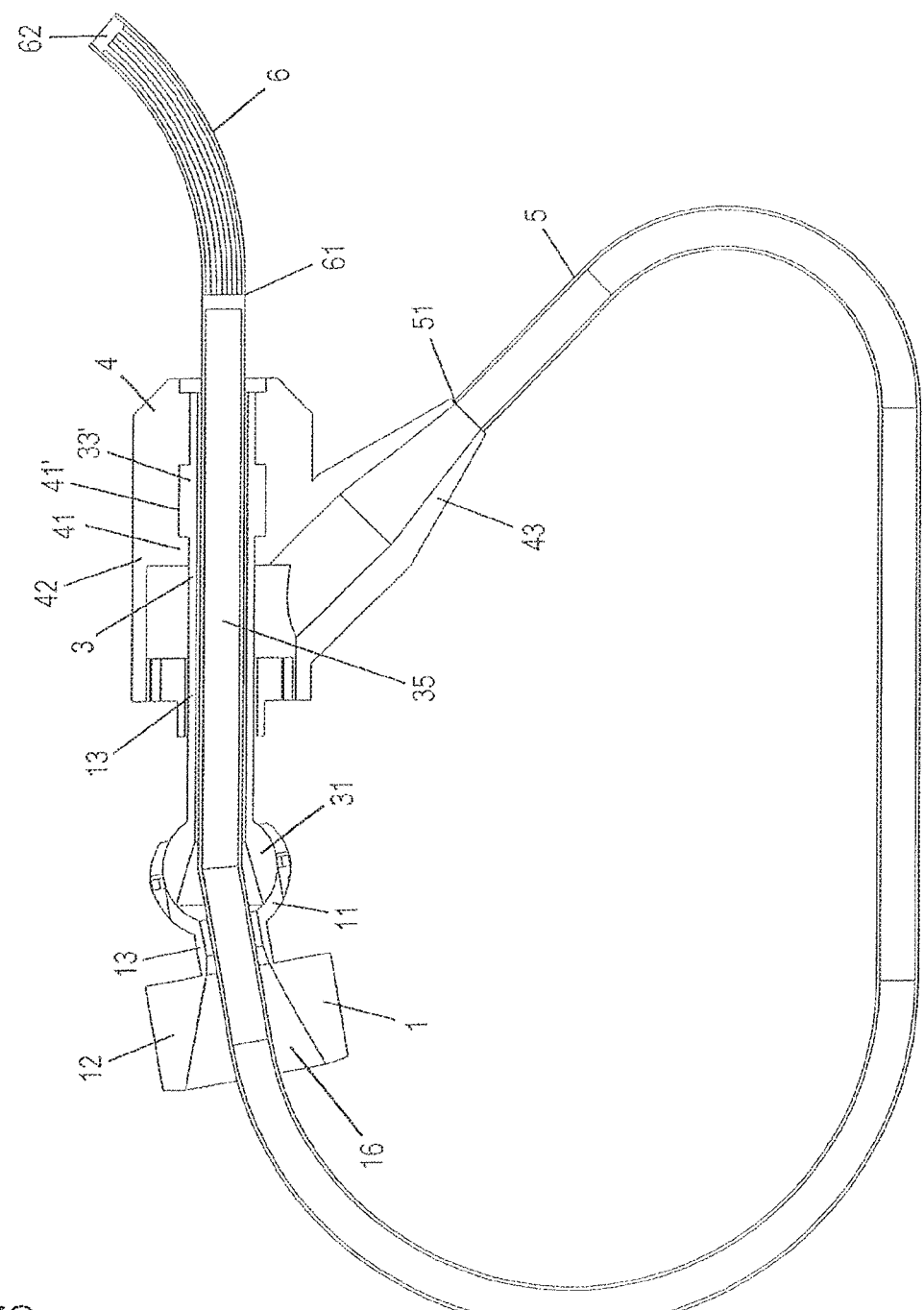
FIG. 6 shows a schematic sectional view of the deflection movement transmission means of FIG. 1 with the catheter tube being passed through the deflection movement transmission means and being deflected to the left.
Figure 7:
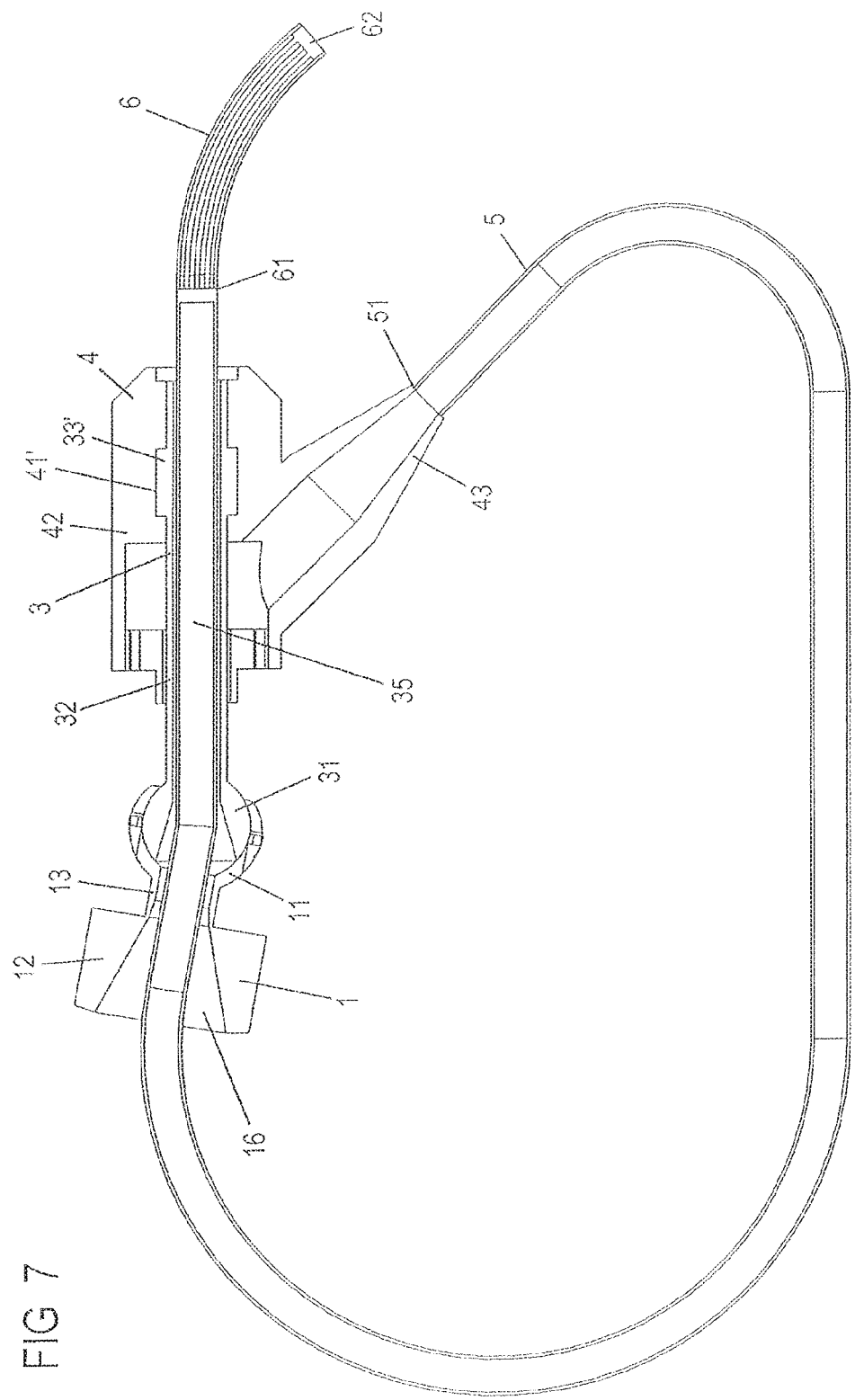
FIG. 7 shows a schematic sectional view of the deflection movement transmission means of FIG. 1 with the catheter tube being passed through the deflection movement transmission means and being deflected to the right.

In a schematic perspective extract-like representation, FIG. 4 shows details of the attachment of the pulling wires to the control pivot member and how the pulling wires are guided to the catheter tube. For reasons of better clarity, the front-left pulling wire 2 has been omitted in FIG. 4.

As it is shown in FIG. 4, several fitting recesses 14 are provided on the outer circumferential surface of the hollow ball portion 11 on the equatorial line of the hollow ball portion 11. Here, four fitting recesses 14 are provided on the hollow ball portion 11. Specifically, the fitting recesses 14 are recesses that are formed into the hollow ball portion 11 and have a circular cross-section and a bottom on which a barrel nipple 21 of the pulling wire 2 can be supported. When the fitting recess 14 is produced, the hollow ball portion 11 can be drilled from the proximal side so that the fitting recess is created as a laterally open blind hole on the outer circumferential surface of the hollow ball portion 11. Any other manufacturing methods are possible here. For example, an injection molding process can be applied. The outer diameter of the fitting recess 14 is selected such that the barrel nipple 21 of the pulling wire 2 fits into the fitting recess 14. On the bottom of the fitting recess 14, i.e. at the distal end of the fitting recess 14, a channel 15 is formed as pulling wire fitting opening, the channel having a diameter larger than the outer diameter of the pulling wire 2, but smaller than the outer diameter of the barrel nipple 21 of the pulling wire 2. In other words, the fitting recess 14 and the pulling wire fitting opening 15 are provided, similar to Bowden cable fittings on bicycles, such that a barrel nipple 21 of a pulling wire 2 can be fitted therein (hooked in). In the fitted state of the pulling wire 2, the barrel nipple constitutes the proximal end of the pulling wire 2.

Figure 2:
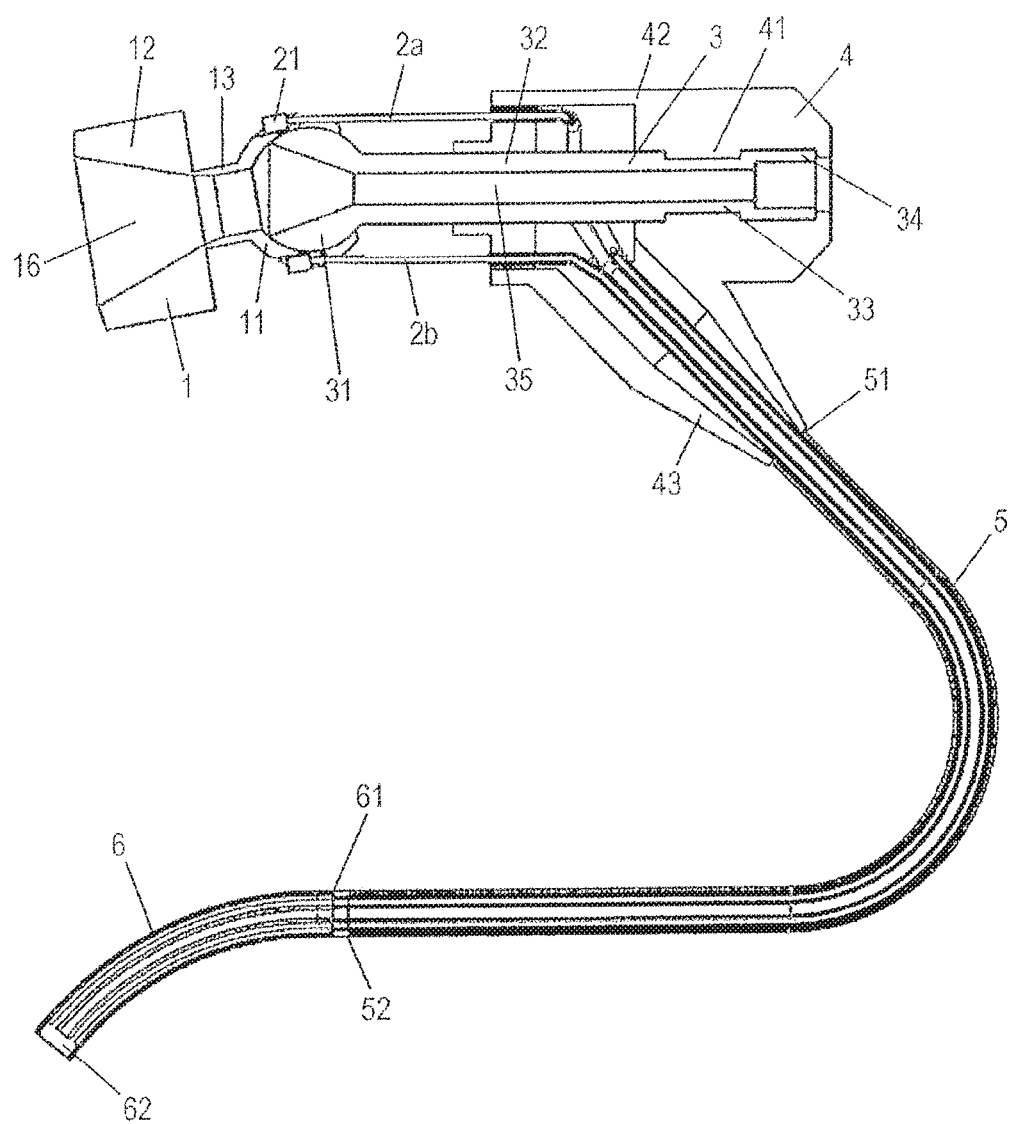
FIG. 2 shows a schematic sectional view of the deflection movement transmission means of FIG. 1 when deflected to the left.
Figure 3:
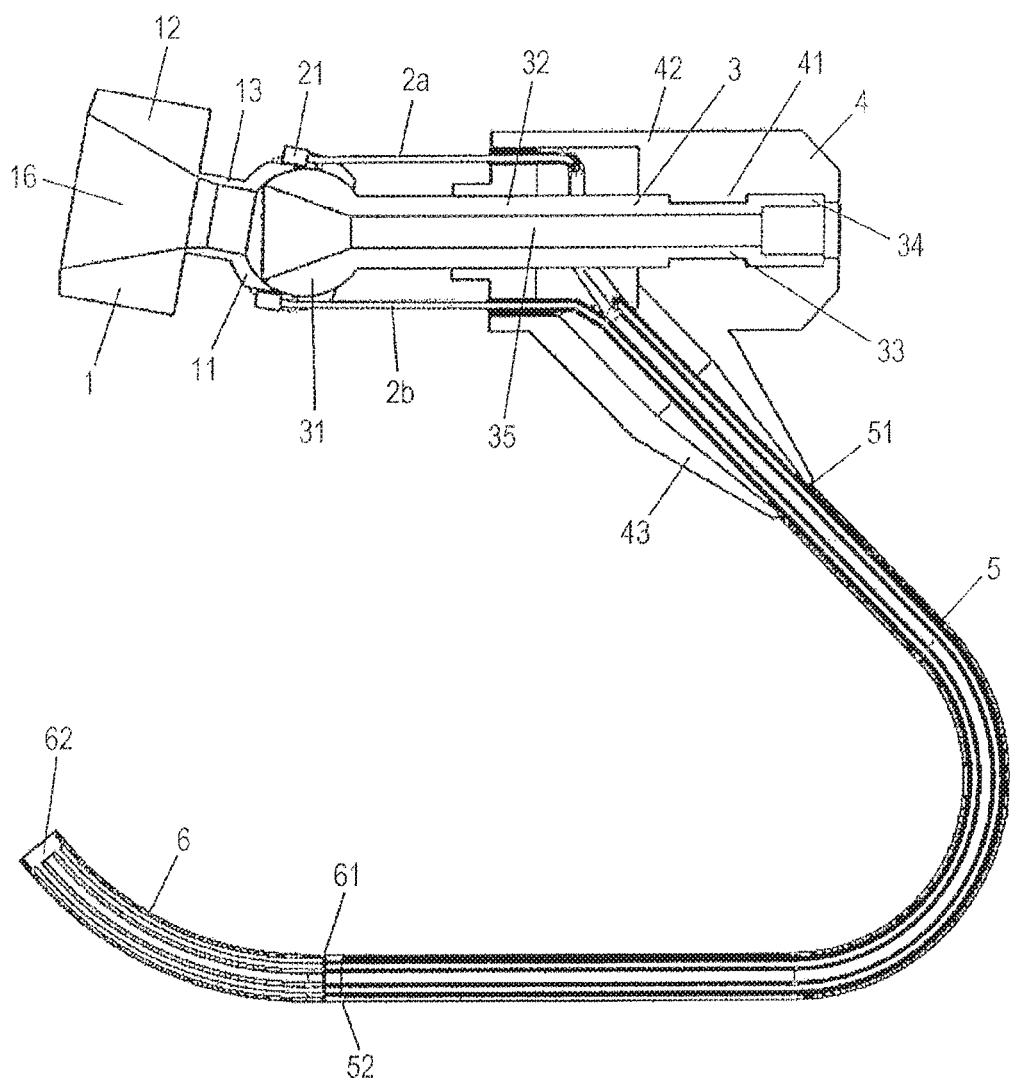
FIG. 3 shows a schematic sectional view of the deflection movement transmission means of FIG. 1 when deflected to the right.

In the present embodiment, four pulling wires 2 are provided, two of which, namely pulling wire 2a and pulling wire 2b, are shown in each of FIGS. 1 to 3. The number of pulling wires 2 is not limited here. One pulling wire 2, two, three, four or more pulling wires may be provided. In case two or more pulling wires 2 are provided, the respective fitting recesses 14 are arranged equally spaced apart from each other at the equator of the hollow ball portion 11.

As it is shown in FIG. 4, on its proximal end, i.e. on its end facing towards the control pivot member 1, the cylinder element 42 comprises the opening to the cylinder element cavity. A pulling wire guiding ring 7 can be inserted into this opening such that the proximal surface, i.e. the surface of the pulling wire guiding ring 7 facing towards the control pivot member 1, is flush with the proximal front face of the cylinder element 42, i.e. the face pointing towards the control pivot member 1. The pulling wire guiding ring 7 is provided with the same number of tangential slits as there are pulling wires 2, as it is shown in FIG. 4. Pulling wire guiding openings 71 extending coaxially with respect to the common axis of the control pivot member 1, the rod element 3 and the cylinder element 42 of the rod element holder 4 are bored in the slits. More precisely, the distance between each fitting recess 14 and the center axis of the control pivot member 1 is the same as the radial distance between the pulling wire guiding bore 71 and the center axis of the pulling wire guiding ring 7.

The pulling wires 2 are passed through the catheter tube 5 and the ring 52 of the catheter tube and are anchored to the deflecting cap 62 of the deflecting portion 6. In particular, the pulling wires 2 are anchored to the deflecting cap 62 such that they are arranged, i.e. fastened, equally spaced apart from each other and in the same order as on the hollow ball portion 11.

The ring 52 comprises openings for the pulling wires 2 in a manner corresponding to the design of the pulling wire guiding ring 7. The length of each pulling wire 2 from the fastening point on the deflecting cap 62 to the fastening point on the pivot portion is always the same.

The ring 52 may as well be omitted.

General Functioning

The control pivot member 1 can be operated like a joystick, wherein its hollow ball portion 11 can be moved on the counter ball portion 31 of the rod element 3. Thus, a pivoting process of the joystick 1 relative to the rod element 3 in any direction is possible. The direction and the extent of the deflection movement of the joystick 1 relative to the rod element 3 is then transmitted to the deflecting portion 6 designed as a bendable body by means of the pulling wires 2 arranged on the deflecting cap 62. In other words, when the joystick 1 is moved to the left relative to the rod element 3, the deflecting portion performs a movement directed to the left, as it is shown in FIG. 2. When the joystick 1 is moved to the right, relative to the rod element 3, the deflecting portion performs a movement directed to the right, as it is the case in FIG. 3.

The control pivot member 1 is put in a straight position prior to inserting the deflecting portion 6, so that the deflecting portion 6 and the portion of the catheter tube 5 adjacent to the deflecting portion 6 are aligned straight. The distal end (on the deflecting cap 62) of the deflecting portion 6 is inserted into the funnel-like insertion opening of the inner channel 16 in the control pivot member 1, advanced through the inner channel 16, inserted in the funnel-like insertion opening of the inner channel 35 in the rod element 3 and advanced through the inner channel 35 until the deflecting portion 6 emerges on the exit opening of the inner channel 35 opposite to the funnel-like insertion opening of the inner channel 35.

When the deflecting portion 6 has reached its intended operational position, i.e. the position in which it is slid through the deflection movement transmission means, the deflecting portion 6 can be brought into the desired position by means of pivoting the control pivot member 1 in the desired direction and by the desired extent. The control pivot member 1 as a joystick can pivot in all directions and, thus, the deflecting portion 6 cannot only pivot to the right and to the left, but in all directions.

First Embodiment

Figure 8:
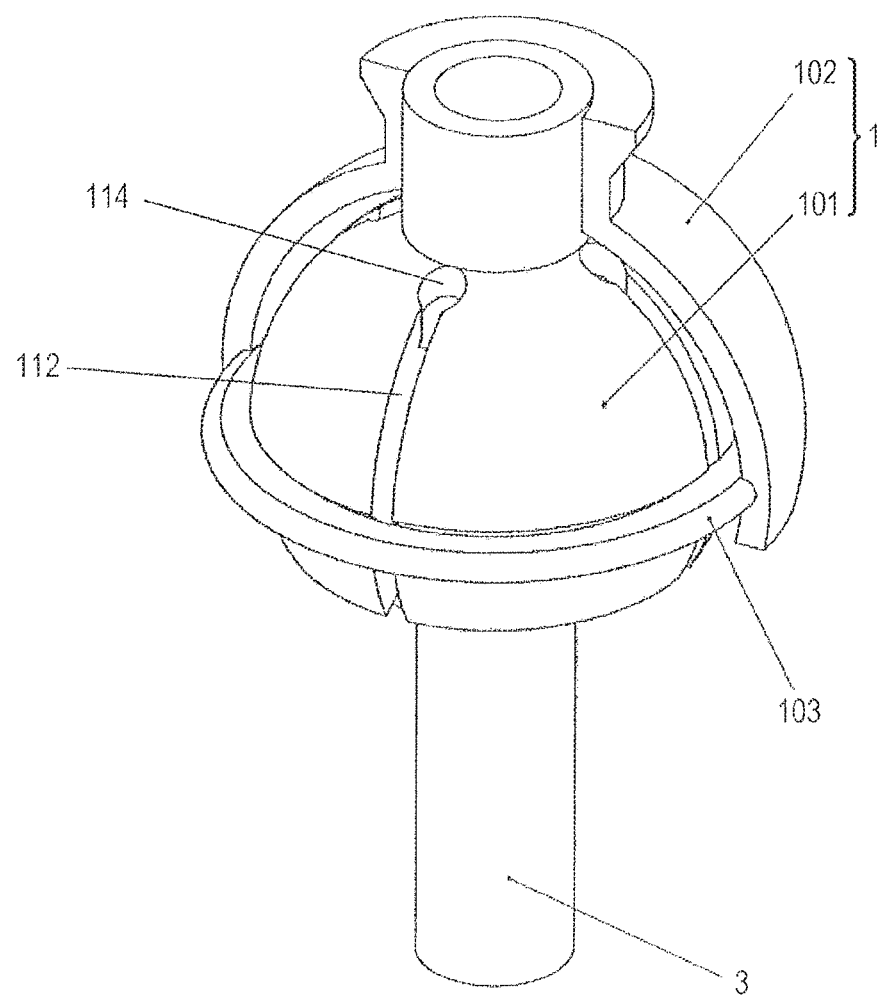
FIG. 8 shows a perspective view of the deflection movement transmission means of a first embodiment.
Figure 9:
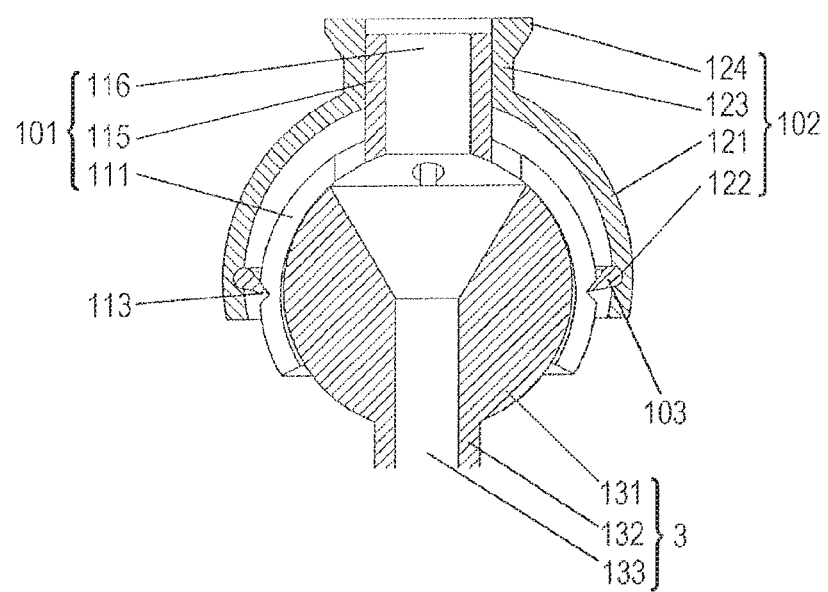
FIG. 9 shows a schematic sectional view of the deflection movement transmission means of the first embodiment.
Figure 10:
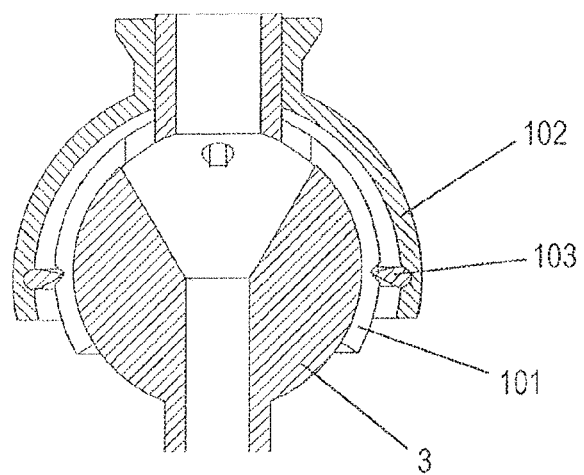
FIG. 10 shows a schematic sectional view of the deflection movement transmission means of the first embodiment.

A first embodiment is shown in FIGS. 8 to 11. FIGS. 8 to 10 show the more detailed design of the deflection movement transmission means of the first embodiment.

The subsequently described design of the deflection movement transmission means of the first embodiment according to FIGS. 8 to 11 can be applied to the general design of a deflection movement transmission means according to FIGS. 1 to 7.

In the present embodiment, the control pivot member 1 comprises, on its distal side, an inner cover body 101 having a bell shape that is slipped onto a ball head 131 on the proximal side of the base body 3. Thus, the inner cover body 101 can be pivoted relative to the ball head 131 of the base body 3. More precisely, the inner cover body 101 comprises an inner shell 111 that forms the bell shape and is placed on the ball head 131, and a pivot lever portion 115 that is attached as a tube portion on the inner shell 111 and extends in the direction facing away from the ball head 131. The inner shell 111 and the pivot lever portion 115 are integrally formed. The inner shell 111 is a partial ball surface body having a constant wall thickness, as is shown in FIGS. 9 and 10. Thus, the inner shell 111 comprises an inner circumferential surface and an outer circumferential surface. In the assembled state of FIGS. 9 and 10, the inner circumferential surface of the inner shell 111 faces towards the ball head 131 and the outer circumferential surface of the inner shell 111 faces away from the ball head 131. The radius of the inner circumferential surface of the inner shell 111 is slightly larger than the radius of the outer circumferential surface of the ball shape of the ball head 131.

As it becomes apparent from FIGS. 9 and 10, the partial ball surface body of the inner shell 111 is not a complete partial ball surface body, but is open on the distal side and provided with an opening for accommodating the pivot lever portion 115 on the proximal side. Thus, the inner shell 111 forms an almost hollow spherical segment or a hollow spherical disc with a constant wall thickness. The distal opening of the inner shell 111 is provided in such a manner that the partial ball surface body of the inner shell 111 is cut off on the distal side of the equator of the inner shell 111, as it is shown in FIGS. 9 and 10. At the proximal opening provided on a pole of the inner shell 111, the pivot lever portion 115 formed as a pipe is inserted such that the distal end of the pivot lever portion 115 formed as a pipe does not protrude beyond the inner circumferential surface of the inner shell 111.

The pivot lever portion 115 extends radially from the inner shell 111. In other words, the extended imagined center line of the pivot lever portion 115 formed as pipe portion extends through the center of the inner shell 111. The pivot lever portion 115 is formed as a cylinder pipe and includes an inner circumferential surface and an outer circumferential surface. The inner circumferential surface of the pivot lever portion 115 forms an inner channel 116. The outer circumferential surface of the pivot lever portion 115 forms a sliding surface for a subsequently described sleeve portion 123.

The inner shell 111 and the pivot lever portion 115 can be made of the same elastic material, preferably an elastic plastic material. Alternatively, the inner shell 111 and the pivot lever portion 115 can be made of different materials. In this case, the inner shell 111 consists of an elastic material, preferably an elastic plastic material, and the pivot lever portion 115 can be made of a stiff (non-elastic) material, preferably a non-elastic plastic material. Preferentially, a plastic material that is easy to clean, injection-moldable and is normally used for medical purposes is used.

The inner shell 111 comprises grooves 112 extending in the direction of the meridians. The grooves 112 are formed on the outer circumferential surface of the inner shell 111 and extend from the distal end of the inner shell 111 in the meridian direction as far as beyond the equator of the inner shell 111. The inner circumferential surface of the inner shell 111 forms a groove bottom.

In the present embodiment, the grooves 112 end just before the proximal opening, i.e. just before the pivot lever portion 115, as can be seen in FIG. 8.

In the present embodiment, four grooves 112 are provided. However, two, three, five or more grooves can be provided, as well. Even a design including only one groove 112 would be possible, although not preferred.

At the proximal end of each groove 112, openings are formed as anchorings 114 for the end holding bodies (formed e.g. as a barrel nipple) of the pulling wires 2. Every anchoring 114 is provided as a through-opening in the inner shell 111. The shape of the anchoring 114 is adapted to the shape of the applied end holding body of the pulling wires 2, which is e.g. designed as a barrel nipple, as shown in FIG. 4.

The anchoring 114 does not have to be a through-opening but may also be designed as a blind hole on the outer circumferential surface of the inner shell 111.

The grooves 112 form wire guides for pulling wire bodies (not shown) on the outer circumferential surface of the inner shell 111 and guide the pulling wire 2 along the outer circumferential surface of the inner shell 111.

Instead of the grooves 112, the inner shell 111 may alternatively comprise slits extending in the direction of the meridians and replacing the grooves 112. Thus, the slits extend from the distal end of the inner shell 111 in the meridian direction as far as beyond the equator of the inner shell 111.

In the present embodiment, the slits also end just before the proximal opening, i.e. just before the pivot lever portion 115. In other words, the inner shell 111 is sliced up by the slits in the meridian direction.

In the present embodiment, four slits are provided. However, two, three, five or more slits can be provided as well. Even a design including only one slit is possible.

The slits facilitate an elastic pressing of the inner shell 111 against the ball head 131.

At the proximal end of each slit, openings 114 preventing the inner shell 111 from tearing open in the proximal direction are formed.

The openings 114 can also be used as anchorings 114 for the end bodies of the pulling wires 2. In this case, every opening 114 is formed as a blind hole on the outer circumference of the inner shell 111 and forms a (e.g. circular) recess that is in cross section adapted to the shape of a barrel nipple and has a bottom on which a barrel nipple of the pulling wire 2 can be supported.

The outer diameter of the opening 114 is chosen such that the barrel nipple 21 of the pulling wire 2 fits into it. A small through-opening is formed on the bottom of the opening 114, the through-opening having a diameter larger than the outer diameter of the pulling wire 2, but smaller than the outer diameter of the barrel nipple of the pulling wire 2.

The inner shell 111 has a V-groove 113 on its outer circumferential surface on the equator. A subsequently described press-on body 103 is inserted into the V-groove 113.

Moreover, on the outside of the inner cover body 101, the control pivot member 1 includes an outer cover body 102 having a bell shape that is slipped onto the inner cover body 101. The outer cover body 102 can be pivoted together with the inner cover body 101 relative to the ball head 131 of the base body 3. More precisely, the outer cover body 102 comprises an outer shell 121 that forms the bell shape and surrounds the inner shell 111 of the inner cover body 101, and a sleeve portion 123 provided as pipe portion on the outer shell 121 and extending in the direction facing away from the ball head 131. The outer shell 121 and the sleeve portion 123 are integrally formed. Similar as the inner shell 111, the outer shell 121 is a partial ball surface body with a constant wall thickness, as it is shown in FIGS. 9 and 10. Thus, the outer shell 121 includes an inner circumferential surface and an outer circumferential surface. In the assembled state of FIGS. 9 and 10, the inner circumferential surface of the outer shell 121 faces towards the inner shell 111 and the outer circumferential surface of the outer shell 121 faces away from the inner shell 111. The inner circumferential surface of the outer shell 121 is spaced apart from the outer circumferential surface of the inner shell 111 by a predetermined extent.

As it can be seen from FIGS. 9 and 10, the partial ball surface body of the outer shell 121 is not a complete partial ball surface body either, but is open on the distal side and provided with an opening for accommodating the sleeve portion 123 on the proximal side. Thus, the outer shell 121 almost forms a hollow spherical segment or a hollow spherical disc having a constant wall thickness. The distal opening of the outer shell 121 is provided such that the partial ball surface body of the outer shell 121 is cut off on the distal side of the equator of the outer shell 121, as is shown in FIGS. 9 and 10. At the proximal opening provided on a pole of the outer shell 121, the sleeve portion 123 formed as a pipe is inserted such that the distal end of the sleeve portion 123 formed as a pipe does not protrude beyond the inner circumferential surface of the outer shell 121.

The sleeve portion 123 extends radially from the outer shell 121. The extended imagined center line of the sleeve portion 123 formed as pipe portion extends through the center of the outer shell 121. The sleeve portion 123 is formed as a cylinder pipe and includes an inner circumferential surface and an outer circumferential surface. The inner circumferential surface of the sleeve portion 123 forms an inner channel. The inner circumferential surface of the inner channel of the sleeve portion 123 is slidable relative to the outer circumferential surface of the pivot lever portion 115.

Thus, the outer cover body 102 can be moved relative to the inner cover body 101 by the sleeve portion 123 sliding on the outer circumference of the pivot lever portion 115. When the outer cover body 102 is moved towards the inner cover body 101, the region of the inner shell 111 adjacent to the pivot lever portion 115 forms a stop for the inner circumferential surface of the outer shell 121 and an end point of the movement of the outer cover body 102 towards the inner cover body 101.

When the outer cover body 102 is moved along the axis of the pivot lever portion 115 relative to the inner cover body 101, two intrinsically stable end positions are achieved. Of these end positions, a first end position (cf. FIG. 9) corresponds to the non-pressed-on position in which the inner shell 111 is not pressed against the ball head 131 of the base body 3, and a second end position (cf. FIG. 10) corresponds to the pressed-on position in which the inner shell 111 is pressed against the ball head 131.

On the end side of the sleeve portion 123 facing away from the outer shell 121, an extended diameter portion 124 is provided on the outer circumferential surface of the sleeve portion 123; this extended diameter portion 124 can also be formed as a flange extending away from the sleeve portion 123. The extended diameter portion 124 or the flange at the sleeve portion 123 make it easier to grip the sleeve portion 123 and to move the outer cover body 102 relative to the inner cover body 101.

The outer shell 121 and the sleeve portion 123 can be made of the same elastic material, preferably a plastic material. Alternatively, the outer shell 121 and the sleeve portion 123 can be made of different materials. Preferably, the outer shell 121 consists of a rigid (non-elastic) material, preferentially a non-elastic plastic material. Preferably, an injection-moldable plastic material that is easy to clean and is normally used for medical purposes is used for the outer shell 121 and the sleeve portion 123.

On its inner circumferential surface, the outer shell 121 includes an annular groove 122 on its equator. A subsequently described press-on body 103 is inserted into the annular groove 122.

Figure 11:
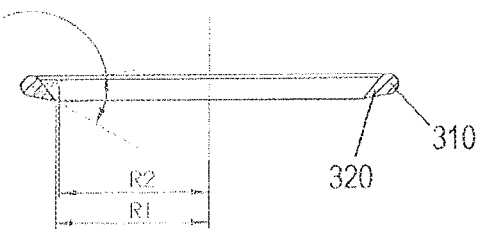
FIG. 11 shows a schematic sectional view of a press-on body of the deflection movement transmission means of the first embodiment.

FIG. 11 shows a schematic sectional view of the press-on body 103 of the deflection movement transmission means of the first embodiment.

The press-on body 103 is formed of an annular member 310 and a toggle lever element 320 integrally formed on the annular member 310. The toggle lever element 320 extends inwards from the annular member 310. Preferably, the toggle lever element 320 does not extend inwards from the annular member 310 in a vertical or centrally perpendicular manner in the median plane of the annular member 310, but the extension direction of the toggle lever element 320 from the annular member 310 is at a predetermined angle to the median plane of the annular member 310, as it is shown in FIG. 11.

The annular member 310 is provided in a pivotable manner in the annular groove 122 that is provided on the inner surface of the outer shell 121 and adapted to the annular shape of the annular member 310.

The tip of the toggle lever element 320 facing away from the annular member 310 is provided in the V-groove 113 of the outer surface of the inner shell 111.

The press-on body 103 can snap between two end positions. The first end position is the position in which it does not load the inner shell 111. The first end position is shown in FIG. 10. The second end position is the position in which the press-on body loads the inner shell 111. The second end position is shown in FIG. 9 and FIG. 11. In the first end position, the tip of the toggle lever element protrudes further inwards than in the second end position; to express it differently: R2<R1 according to FIG. 11.

Specific Functioning

FIG. 9 shows the unlocked position of a control pivot member (joystick) 1 relative to the base member 3; in other words, the unlocked position of the inner shell 111 relative to the ball head 131. In a specific achievable position of the control pivot member 1 relative to the base member 3, this pivot position shall be locked. In the course of this, the outer cover body 102 is moved downwards relative to the inner cover body 101, i.e. in the distal direction as far as the stop. Thus, the annular groove 122 moves on the inner surface of the outer shell 121 in the distal direction as far as beyond the V-groove 113 of the outer surface of the inner shell 111. In this way, the press-on body 103, whose annular member 310 is provided in a pivotable manner in the annular groove 122, which is provided in the inner surface of the outer shell 121 and adapted to the annular shape of the annular member 310, is pivoted relative to the outer shell 121. Thus, in the course of this pivoting, the press-on body 103, similar to a toggle lever, is brought into a position in which the tip of the toggle lever element 320 facing away from the annular member 310 is almost on the center plane of the annular member 310. Thus, the region of the inner shell 111 on which the V-groove 113 is formed, is pushed inwards towards the ball head 131 and held there by means of the press-on member 103.

FIG. 10 shows the locked position of the control pivot member 1 relative to the base member 3; in other words, the locked position of the inner shell 111 relative to the ball head 131.

By moving the outer cover body 102 relative to the inner cover body 101 upwards, i.e. in the proximal direction, the position is unlocked, that is the locking is released again, since the annular groove 122 of the outer shell 121 moves in the proximal direction as far as beyond the V-groove 113 of the outer surface of the inner shell 111. Thus, the press-on body 103 is turned relative to the outer shell 121. Finally, the press-on body 103 reaches a position in which the tip of the toggle lever element 320 facing away from the annular member 310 is angularly aligned to the center plane of the annular member 310 at the predetermined angle. In this way, the load applied by the press-on body 103 to the region of the inner shell 111 on which the V-groove 113 is formed, is reduced. In the region of the inner shell 111 in which the V-groove 113 is formed, the inner shell 111 moves away from the ball head 131. The locking of the control pivot member 1 relative to the base member 3 is thus released.

Second Embodiment

Figure 12:
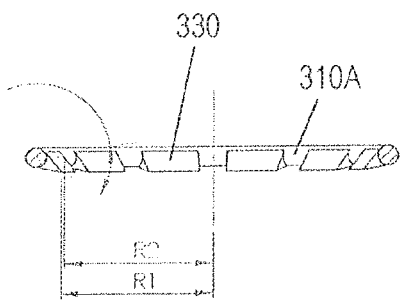
FIG. 12 shows a schematic sectional view of a press-on body of the deflection movement transmission means of a second embodiment.

FIG. 12 shows a schematic sectional view of a press-on body of the deflection movement transmission means of a second embodiment.

In the first embodiment, the press-on body 103 is formed of an annular member 310 and a toggle lever element 320 integrally formed on the annular member 310.

In the second embodiment, the toggle lever element of the press-on body 103 is formed of toggle lever element segments 330 integrally formed on the annular member 310A. The extension direction of the toggle lever element segments 330 is the same as in the first embodiment. The individual toggle lever element segments 330 are arranged equally spaced apart on the inner circumference of the annular member 310A and point inwards.

In the first embodiment, the press-on body 103 is quasi formed as a snap ring comprising a toggle lever element. In the second embodiment, it is already sufficient when partial regions of the toggle lever element, namely a single toggle lever element segment 330 or several toggle lever element segments 330 snap without all of the toggle lever element segments 330 having to snap.

The number of toggle lever element segments 330 is not limited and can be four or less or more.

Otherwise, the function is similar as in the first embodiment. Incidentally, the design of the first embodiment can be understood in such a manner that it comprises an indefinite number of toggle lever element segments if the press-on body is formed elastically.

Advantages of the Invention

With the inner shell 111, the deflection movement transmission means of the present invention uses an elastic member acting as friction component on an inner ball element of a joystick. The press-on body 103 including the toggle lever element forms an elastic ring that, like a "frog clicker" or a snap switch, turns inside out and presses the inner shell 111 to the ball head 131, thereby locking the inner shell 111 on the ball head 131. Thus, the achieved pivot position of the control pivot member (joystick) 1 relative to the base member 3 can be easily and safely locked.

The present invention can be advantageously used in an endoscope formed as a duodenoscope.

The costs of manufacturing the deflection movement transmission means can be kept very low due to the simple design. The deflection movement transmission means can be designed as a single-use device.

Further Alternatives

A pulling wire end body in the form of a barrel nipple can be fitted into the anchoring 114 shown in FIG. 8. The invention is not restricted to a barrel nipple and the pulling wire end body may be formed as a known pear nipple; any similar nipples can be applied. The shape of the anchoring 114 can be adapted to the selected shape of the pulling wire end body.

In the first embodiment, the size of the inner shell 111 in FIGS. 8 to 10 has been chosen such that it comprises a distal opening of approximately 120°.

The invention is not restricted thereto. Any hollow ball shape size of the inner shell 111 can be chosen as long as the same is still able to perform the pivot movement on the ball head 131 and can be pressed against the ball head 131. The inner shell 111 could also have the shape of a hollow ball ring portion which extends by a predetermined minimum extent in parallel to the axial direction of the control pivot member 1 to both sides of the equatorial line and practically forms an equatorial belt.

On the outer circumference of the rod portion 132 of the base member 3, loops that are spaced apart from the inner cover body 101 and can contain a pulling wire 2 can be provided on respective imagined extensions of the groove 112 or the corresponding slit. The loops are provided in the same number as there are pulling wires 2 and have a similar task as the previously described pulling wire guiding ring 7.

In the first embodiment, the inner shell 111 comprises the V-groove 113 on its outer circumferential surface on the equator, and the outer shell 121 comprises an annular groove 122 on its inner circumferential surface on the equator. The principle of the invention can also be applied to a design in which the V-groove 113 extends in a manner offset from and in parallel to the equator, and/or the annular groove 122 extends in a manner offset from and in parallel to the equator.

In the first embodiment, the inward-facing tip of the press-on body 103 formed as a toggle lever element engages with the V-groove 113 of the inner shell 111. Here, the press-on body 103 and the inner shell 111 are formed separately. Alternatively, the tip of the press-on body 103 formed as a toggle lever element can be molded like a hinge on the bottom of the V-groove 113 of the inner shell 111, which means that the press-on body 103 and the inner shell 111 are integral. Then, the press-on body 103 acts on the bottom of the V-groove 113 like a hinge lip.

In the first and second embodiments, the press-on body 103 is inserted into the V-groove 113 and formed as a ring with the toggle lever element 320 or the toggle lever element segment 330. In an alternative, the press-on body is not a continuous ring, but consists of (for example, four or more or less) individual separate ring portions (equally distributed on the circumference), which are anchored to the inner shell 111 and/or the outer shell 121. The separate ring portions can, for example, be molded to the inner shell 111 and/or the outer shell 121 and, thus, be integral therewith.

In another alternative, the press-on body is not made of individual separate ring portions, but of (for example four or more or less) individual separate struts (equally distributed on the circumference), which are anchored to the inner shell 111 and/or the outer shell 121 and extend between the inner shell 111 and the outer shell 121.

The anchoring of the press-on body 103 to the inner shell 111 and the outer shell 121, shown in the embodiments, is not restricted to the groove and the recess. Any anchoring of the press-on body 103 to the inner shell 111 and the outer shell 121 by which a toggle lever function is ensured can be applied.

In another alternative, the outer cover body 102 can be omitted. In order to nevertheless support the press-on body, a lever mechanism by which the press-on body can be operated so as to press the inner shell 111 against the ball head 131 is attached to the outer surface of the inner shell 111 facing away from the ball head 131. Such a lever mechanism can be provided as a kind of toggle lever mechanism in which a rigid support foot extends radially from the inner shell 111. A side strut extending in the lateral direction relative to the support foot is rigidly attached on the side of the support foot remote from the inner shell 111. The support foot and the side strut form a gallows. An articulation point to which a press-on body is movably fastened is provided on the side of the side strut remote from the support foot. The press-on body can pivot relative to the support foot and the side strut. The press-on body is longer than the support foot and can press a region of the inner shell 111 against the ball head 131.

In an especially simple alternative, the outer cover body 102 can be omitted and the press-on body can be formed by a simple pipe having an inner diameter size that corresponds to the outer diameter of the ball head 131 plus twice the wall thickness of the inner shell 111 plus a potential optional clearance. The pipe extends in parallel to the control pivot member 1 and is slid on the inner shell 111 for locking the pivot position of the control pivot member, wherein the inner shell is pressed against the ball head 131.

In the embodiment, the pulling wires 2 are anchored to the inner shell 111. In an alternative, the pulling wires 2 can be anchored to the outer shell 121. In this case, grooves following the principle of the grooves 112 of FIG. 8 can be provided on the outer surface of the outer shell 121.

In the embodiments, the inner shell 111 and the outer shell 121 have a continuous wall thickness. Alternatively, the wall thickness of the inner shell 111 and/or the outer shell 121 can become thicker or thinner in the meridian direction and/or in the direction perpendicular to the meridian direction.

The inner circumferential surface of the inner channel of the sleeve portion 123 of the outer cover body 102 is slidable relative to the outer circumferential surface of the pivot lever portion 115 of the inner cover body 101. In another embodiment, the pivot lever portion 115 of the inner cover body 101 can be proximally extended (relative to the representation in FIGS. 9 and 10) and, on the end side of the pivot lever portion 115 facing away from the inner shell 111, it can comprise a radially extending stop on the outer circumferential surface of the pivot lever portion 115, the stop forming an end point of the vertical movement of the outer cover body 102 when the stop gets into contact with the proximal end side of the sleeve portion 123.

Moving the outer cover body 102 relative to the inner cover body 101 can be effected manually by acting on the extended diameter portion or on the flange of the sleeve portion 123. Alternatively, the principle of a threaded rod and a nut can be applied, wherein a proximal extension of the pivot lever portion 115 can have an outer thread on which a nut operatively coupled with the sleeve portion 123 is threadably provided and can move the sleeve portion 123.

In the embodiments, the annular member 310 is provided in a pivotable manner in the annular groove 122 of the inner surface of the outer shell 121 and the tip of the toggle lever element 320 facing away from the annular member 310 is provided in the V-groove 113 of the outer surface of the inner shell 111. This principle may be inverted. This means, alternatively, the annular member 310 can be provided in a pivotable manner in a groove provided on an outer surface of the inner shell 111 facing towards the outer shell 121, and adapted to the annular shape of the annular member 310, and the tip of the toggle lever element 320 facing away from the annular member 310 can be provided in a V-groove of an inner surface of the outer shell 121 facing towards the inner shell 111.

In the embodiments, the deflection movement transmission means is used in an endoscope deflecting control means in an endoscope. The deflection movement transmission means can also be used in other technical fields. A use in water-conducting channels, in mining tunnels, etc. is also possible. The invention can be used in any situation where pivot movements are transformed into deflection movements of a deflection element.

LIST OF REFERENCE SIGNS 1 control pivot member; joystick
2, 2a, 2b pulling wire
3 base member; rod element
4 rod element holder
5 catheter tube
6 bendable body, deflecting portion
7 pulling wire guiding ring
11 hollow ball portion
11A foot surface of the hollow ball portion 11
12 head of the control pivot member 1
13 rod portion
14 fitting recess/hook-in recess
15 pulling wire fitting opening
16 inner channel in the control pivot member
21 barrel nipple
31 head portion; counter ball portion
31A front face of the head portion 31
32 longitudinal cylinder
33 threaded portion of the rod element 3
34 square end; distal end of the rod element 3
35 inner channel in the rod element
41 threaded portion of the rod element holder 4
42 cylinder element
43 catheter connecting element
51 catheter tube connection
52 ring
61 deflecting connection
62 deflecting cap
71 pulling wire guiding bore
72 threaded hole for a fixing screw
101 inner cover body
102 outer cover body
103 press-on body
111 inner shell
112 groove
113 V-groove
114 anchoring for pulling wire body
115 pivot lever portion
116 inner channel
121 outer shell
122 annular groove
123 sleeve portion
124 extended diameter portion, flange
131 ball head
132 rod portion
133 inner channel
310, 310A annular member
320 toggle lever element
330 toggle lever element segment

The invention claimed is:

1. A deflection movement transmission system comprising:
a control pivot for effecting a deflection movement; and
a base body including a ball head on which the control pivot for effecting a deflection movement is arranged such that a pivot movement of the control pivot can be performed relative to the base body, wherein:
the control pivot includes an inner shell comprising a hollow spherical segment having a distal opening provided such that the hollow spherical segment is cut off on a distal side of the equator of the inner shell, the inner shell being elastic or made of several movable pieces and has an inner surface facing towards the ball head, and
at the outer surface of the inner shell facing away from the ball head, at least one press-on body is provided, by which the inner shell can be pressed against the base body to lock a deflection position of the control pivot.

2. The deflection movement transmission system according to claim 1,
wherein the control pivot comprises a non-elastic outer shell, and
wherein, between the inner shell and the outer shell, the at least one press-on body is arranged, by which the inner shell can be pressed against the base body relative to the outer shell.

3. The deflection movement transmission system according to claim 1, wherein:
the control pivot is arranged at the proximal end of the deflection movement transmission system,
a bendable body to be deflected is arranged at the distal end of the deflection movement transmission system,
pulling wire bodies for deflecting the bendable body to be deflected can be fitted to the control pivot, and
the base body and the control pivot each have an inner channel through which the bendable body to be deflected can be passed.

4. An endoscope bending control system comprising a deflection movement transmission system according to claim 1.

5. An endoscope comprising an endoscope bending control system according to claim 4.

6. A deflection movement transmission system comprising:
a control pivot for effecting a deflection movement and
a base body including a ball head on which the control pivot for effecting a deflection movement is arranged such that a pivot movement of the control pivot can be performed relative to the base body, wherein:
the control pivot comprises an inner shell, which is elastic or made of several movable pieces and has an inner surface facing towards the ball head,
at the outer surface of the inner shell facing away from the ball head, at least one press-on body is provided, by which the inner shell can be pressed against the base body to lock a deflection position of the control pivot,
the control pivot comprises a non-elastic outer shell, wherein, between the inner shell and the outer shell, the at least one press-on body is arranged, by which the inner shell can be pressed against the base body relative to the outer shell,
the at least one press-on body contacts the inner shell and the outer shell, and
the outer shell is movable relative to the inner shell to bring, via the at least one press-on body, the inner shell into the position pressed against the base body.

7. A deflection movement transmission system comprising:
a control pivot for effecting a deflection movement; and
a base body including a ball head on which the control pivot for effecting a deflection movement is arranged such that a pivot movement of the control pivot can be performed relative to the base body, wherein:
the control pivot comprises an inner shell, which is elastic or made of several movable pieces and has an inner surface facing towards the ball head,
at the outer surface of the inner shell facing away from the ball head, at least one press-on body is provided, by which the inner shell can be pressed against the base body to lock a deflection position of the control pivot, the control pivot comprises a non-elastic outer shell, wherein, between the inner shell and the outer shell, the at least one press-on body is arranged, by which the inner shell can be pressed against the base body relative to the outer shell, the inner shell includes a pivot lever extending away from the ball head, and the outer shell is movable relative to the inner shell in the direction of the axis of the pivot lever so as to bring, via the at least one press-on body, the inner shell into the position pressed against the base body.

8. The deflection movement transmission system according to claim 7, wherein the outer shell has two intrinsically stable end positions when moved along the axis of the pivot lever relative to the inner shell, and wherein a first end position corresponds to the non-pressed-on position, in which the inner shell is not pressed against the base body, and a second end position corresponds to the pressed-on position, in which the inner shell is pressed against the base body.

9. A deflection movement transmission system comprising:

a control pivot for effecting a deflection movement; and a base body including a ball head on which the control pivot for effecting a deflection movement is arranged such that a pivot movement of the control pivot can be performed relative to the base body, wherein:

the control pivot comprises an inner shell, which is elastic or made of several movable pieces and has an inner surface facing towards the ball head, at the outer surface of the inner shell facing away from the ball head, at least one press-on body is provided, by which the inner shell can be pressed against the base body to lock a deflection position of the control pivot, and the at least one press-on body includes a toggle lever that is supported in a pivotable manner on the inside of the outer shell and on the outside of the inner shell.

10. The deflection movement transmission system according to claim 9, wherein the toggle levers of multiple press-on bodies are integrally connected by an elastic ring.

11. A deflection movement transmission system comprising:

a control pivot for effecting a deflection movement; and a base body including a ball head on which the control pivot for effecting a deflection movement is arranged such that a pivot movement of the control pivot can be performed relative to the base body, wherein:

the control pivot comprises an inner shell, which is elastic or made of several movable pieces and has an inner surface facing towards the ball head, at the outer surface of the inner shell facing away from the ball head, at least one press-on body is provided, by which the inner shell can be pressed against the base body to lock a deflection position of the control pivot, and the at least one press-on body forms an elastic ring.

* * * * *